(12) United States Patent  (10) Patent No.: US 8,937,900 B2
Chin et al.  (45) Date of Patent: Jan. 20, 2015

(54) ENHANCING PILOT CHANNEL TRANSMISSION IN TD-SCDMA MULTICARRIER SYSTEMS USING SECONDARY CARRIER FREQUENCIES

(75) Inventors: Tom Chin, San Diego, CA (US);
Guangming Shi, San Diego, CA (US);
Kuo-Chun Lee, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 378 days.

(21) Appl. No.: 12/964,487

(22) Filed: Dec. 9, 2010

(65) Prior Publication Data
US 2012/0020283 A1  Jan. 26, 2012

Related U.S. Application Data

(60) Provisional application No. 61/366,073, filed on Jul. 20, 2010.

(51) Int. Cl.
*H04B 7/204* (2006.01)
*C07D 401/06* (2006.01)
*H04L 5/00* (2006.01)
*H04W 4/00* (2009.01)

(52) U.S. Cl.
CPC .............. *C07D 401/06* (2013.01); *H04L 5/001* (2013.01); *H04L 5/0016* (2013.01); *H04L 5/0019* (2013.01); *H04L 5/0048* (2013.01); *H04L 5/005* (2013.01); *H04L 5/0053* (2013.01); *H04W 4/00* (2013.01)
USPC .......................................... 370/319; 370/344

(58) Field of Classification Search
USPC .............. 370/310, 310.2, 312, 328, 338, 319, 370/344
See application file for complete search history.

(56) References Cited

U.S. PATENT DOCUMENTS

| 4,304,000 A | 12/1981 | Bonnerot et al. |
| 5,680,395 A | 10/1997 | Weaver, Jr. et al. |

(Continued)

FOREIGN PATENT DOCUMENTS

| CN | 1722635 A | 1/2006 |
| EP | 0797318 A2 | 9/1997 |

(Continued)

OTHER PUBLICATIONS

Astely, D., et al., "LTE: the evolution of mobile bradband", IEEE Communications Magazine, vol. 47, No. 4, Apr. 1, 2009, pp. 44-51, XP055000053, ISSN: 0163-6804, DOI:10.1109/MCOM.2009.4907406.

(Continued)

*Primary Examiner* — Brenda H Pham
(74) *Attorney, Agent, or Firm* — Kristine U. Ekwueme

(57) ABSTRACT

Wireless communication in a multicarrier radio access network, such as a (TD-SCDMA) network, may be implemented where a user equipment (UE) maintains communication over various carrier frequencies in the multicarrier network. The UE will receive a downlink pilot channel transmitted on every subframe on a primary carrier frequency. The UE will also receive a downlink pilot channel transmitted on less than every subframe on a secondary carrier frequency The downlink pilot channel is sent in subframes on the secondary carrier frequencies using a particular period and offset to reduce or minimize interference.

54 Claims, 10 Drawing Sheets

(56) References Cited

U.S. PATENT DOCUMENTS

| | | | |
|---|---|---|---|
| 6,360,098 | B1 | 3/2002 | Ganesh et al. |
| 6,993,333 | B2 | 1/2006 | Laroia et al. |
| 7,869,416 | B2 | 1/2011 | Ramakrishna et al. |
| 8,204,098 | B2 * | 6/2012 | Kaikkonen et al. ............ 375/147 |
| 8,295,779 | B2 * | 10/2012 | Cave et al. .................... 455/69 |
| 2003/0060200 | A1 | 3/2003 | Soliman |
| 2003/0124994 | A1 | 7/2003 | Ylitalo |
| 2004/0132494 | A1 | 7/2004 | Tirkkonen et al. |
| 2005/0002442 | A1 | 1/2005 | Litwin et al. |
| 2008/0020779 | A1 | 1/2008 | Ode et al. |
| 2008/0159234 | A1 | 7/2008 | Prakash et al. |
| 2009/0161634 | A1 | 6/2009 | Tiedemann, Jr. et al. |
| 2010/0130219 | A1 * | 5/2010 | Cave et al. .................... 455/450 |
| 2010/0273520 | A1 * | 10/2010 | Pelletier et al. ............... 455/522 |

FOREIGN PATENT DOCUMENTS

| | | |
|---|---|---|
| EP | 1324510 A1 | 7/2003 |
| EP | 1946575 A1 | 7/2008 |
| JP | 2006211645 A | 8/2006 |
| RU | 2120702 C1 | 10/1998 |
| WO | 0169949 A1 | 9/2001 |
| WO | 0178254 A1 | 10/2001 |
| WO | 0189112 A1 | 11/2001 |
| WO | 03028400 A1 | 4/2003 |
| WO | 2006113188 A2 | 10/2006 |

OTHER PUBLICATIONS

Ericsson: "Usage of DwPTS", 3GPP Draft; R1-080347, 3rd Generation Partnership Project (3GPP), Mobile Competence Centre ; 650, Route Des Lucioles ; F-06921 Sophia-Antipolis Cedex; France, vol. RAN WG1, No. Sevilla, Spain; 20080109, Jan. 9, 2008, XP050108866, [retrieved on Jan. 9, 2008] 1. Introduction, 3. Collision of PSS and RS/controlsignalling.

International Search Report and Written Opinion—PCT/US2011/044587—ISA/EPO—May 2, 2013.

Ratasuk, R., et al., "TDD design for UMTS Long-Term Evolution", Personal, Indoor and Mobile Radio Communications, 2008, PIMRC 2008. IEEE 19th International Symposium on, IEEE, Piscataway, NJ, USA, Sep. 15, 2008, pp. 1-5, XP031371512, ISBN: 978-1-4244-2643-0 II. LTE air-interface overview IV. TDD Frame structure figures 1,5.

Texas Instruments: "Remaining CSI-RS signaling aspects in Rel-10", 3GPP Draft; R1-105894 TI Remaning Aspects for CSI-RS, 3rd Generation Partnership Project (3GPP), Mobile Competence Centre ;650, Route Des Lucioles ; F-06921 Sophia-Antipolis Cedex ; France, vol. RAN WG1, No. Jacksonville, USA; 20101115, Nov. 9, 2010, XP050466718, [retrieved on Nov. 9, 2010], 1. Introduction, 2. Duty cycle for het-net operation, 3. Collison between CSI-RS andBCH/PSS/SSS/Paging/SIB.

Taiwan Search Report—TW100125660—TIPO—Nov. 19, 2013.

* cited by examiner

Cell A – Primary Carrier on Frequency 1

Cell B – Primary Carrier on Frequency 2

Cell C – Primary Carrier on Frequency 3

|  | Cell A | Cell B | Cell C |
|---|---|---|---|
| Frequency 1 | Primary | Offset = 0 | Offset = 1 |
| Frequency 2 | Offset = 0 | Primary | Offset = 1 |
| Frequency 3 | Offset = 1 | Offset = 0 | Primary |

*FIG. 9*

ENHANCING PILOT CHANNEL TRANSMISSION IN TD-SCDMA MULTICARRIER SYSTEMS USING SECONDARY CARRIER FREQUENCIES

CROSS REFERENCE TO RELATED APPLICATION

This application claims the benefit of U.S. provisional patent application no. 61/366,073 filed Jul. 20, 2010, in the names of CHIN et al., the disclosure of which is expressly incorporated herein by reference in its entirety.

BACKGROUND

1. Field

Aspects of the present disclosure relate generally to wireless communication systems, and more particularly, to enhancing pilot channel transmission in time division-synchronous code division multiple access (TD-SCDMA) multicarrier systems using secondary carrier frequencies.

2. Background

Wireless communication networks are widely deployed to provide various communication services such as telephony, video, data, messaging, broadcasts, and so on. Such networks, which are usually multiple access networks, support communications for multiple users by sharing the available network resources. One example of such a network is the Universal Terrestrial Radio Access Network (UTRAN). The UTRAN is the radio access network (RAN) defined as a part of the Universal Mobile Telecommunications System (UMTS), a third generation (3G) mobile phone technology supported by the 3rd Generation Partnership Project (3GPP). The UMTS, which is the successor to Global System for Mobile Communications (GSM) technologies, currently supports various air interface standards, such as Wideband-Code Division Multiple Access (W-CDMA), Time Division-Code Division Multiple Access (TD-CDMA), and Time Division-Synchronous Code Division Multiple Access (TD-SCDMA). For example, China is pursuing TD-SCDMA as the underlying air interface in the UTRAN architecture with its existing GSM infrastructure as the core network. The UMTS also supports enhanced 3G data communications protocols, such as High Speed Downlink Packet Data (HSDPA), which provides higher data transfer speeds and capacity to associated UMTS networks.

As the demand for mobile broadband access continues to increase, research and development continue to advance the UMTS technologies not only to meet the growing demand for mobile broadband access, but to advance and enhance the user experience with mobile communications.

SUMMARY

In one aspect of the disclosure, a method of wireless communication includes receiving a downlink pilot channel transmitted on a primary carrier during every subframe and periodically receiving the downlink pilot channel on a secondary carrier at a first time offset. The period is longer than one subframe.

In another aspect of the disclosure, a user equipment (UE) configured for wireless communication in a multicarrier radio access network includes means for receiving a downlink pilot channel transmitted on a primary carrier during every subframe. The UE also includes means for periodically receiving the downlink pilot channel on a secondary carrier at a first time offset. The period is longer than one subframe.

In another aspect of the disclosure, a computer program product includes a computer-readable medium having program code recorded thereon. The program code includes code to receive a downlink pilot channel transmitted on a primary carrier during every subframe and program code to periodically receive the downlink pilot channel on a secondary carrier at a first time offset. The period is longer than one subframe.

In another aspect of the disclosure, a UE configured for wireless communication includes at least one processor and a memory coupled to the processor. The processor is configured to receive a downlink pilot channel transmitted on a primary carrier during every subframe and to periodically receive the downlink pilot channel on a secondary carrier at a first time offset. The period is longer than one subframe.

BRIEF DESCRIPTION OF THE DRAWINGS

FIG. 9 is a chart illustrating multi-carrier communications in a TD-SCDMA communication system according to one aspect of the present disclosure.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

Figure 1:
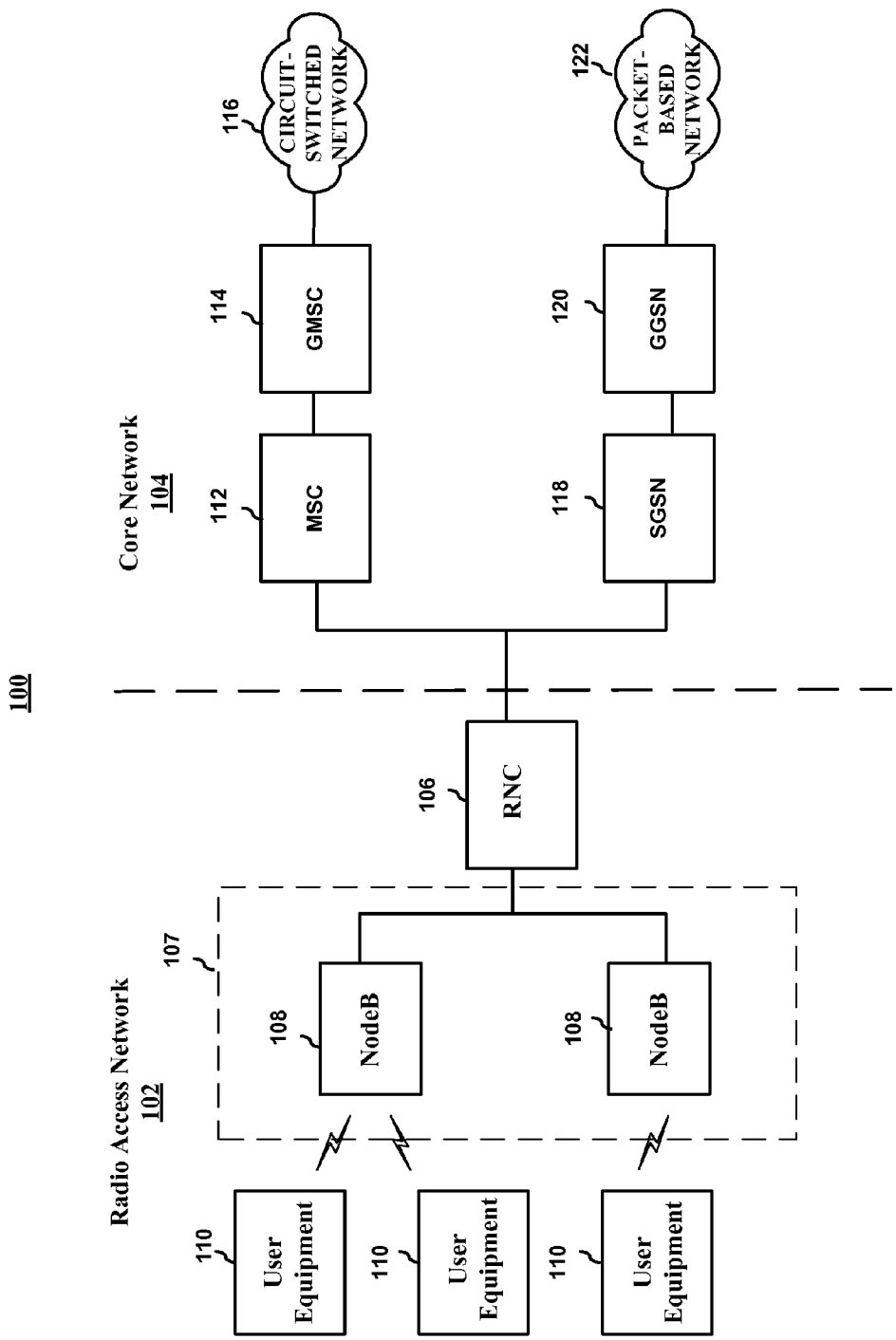
FIG. 1 is a block diagram conceptually illustrating an example of a telecommunications system.

Turning now to FIG. 1, a block diagram is shown illustrating an example of a telecommunications system 100. The various concepts presented throughout this disclosure may be implemented across a broad variety of telecommunication systems, network architectures, and communication standards. By way of example and without limitation, the aspects of the present disclosure illustrated in FIG. 1 are presented with reference to a UMTS system employing a TD-SCDMA standard. In this example, the UMTS system includes a (radio access network) RAN 102 (e.g., UTRAN) that provides various wireless services including telephony, video, data, messaging, broadcasts, and/or other services. The RAN 102 may be divided into a number of Radio Network Subsystems (RNSs), such as an RNS 107, each controlled by a Radio Network Controller (RNC), such as an RNC 106. For clarity, only the RNC 106 and the RNS 107 are shown; however, the RAN 102 may include any number of RNCs and RNSs in addition to the RNC 106 and RNS 107. The RNC 106 is an apparatus responsible for, among other things, assigning, reconfiguring and releasing radio resources within the RNS 107. The RNC 106 may be interconnected to other RNCs (not shown) in the RAN 102 through various types of interfaces, such as a direct physical connection, a virtual network, or the like, using any suitable transport network.

The geographic region covered by the RNS 107 may be divided into a number of cells, with a radio transceiver apparatus serving each cell. A radio transceiver apparatus is commonly referred to as a node B in UMTS applications, but may also be referred to by those skilled in the art as a base station (BS), a base transceiver station (BTS), a radio base station, a radio transceiver, a transceiver function, a basic service set (BSS), an extended service set (ESS), an access point (AP), or some other suitable terminology. For clarity, two node Bs 108 are shown; however, the RNS 107 may include any number of wireless node Bs. The node Bs 108 provide wireless access points to a core network 104 for any number of mobile apparatuses. Examples of a mobile apparatus include a cellular phone, a smart phone, a session initiation protocol (SIP) phone, a laptop, a notebook, a netbook, a smartbook, a personal digital assistant (PDA), a satellite radio, a global positioning system (GPS) device, a multimedia device, a video device, a digital audio player (e.g., MP3 player), a camera, a game console, or any other similar functioning device. The mobile apparatus is commonly referred to as user equipment (UE) in UMTS applications, but may also be referred to by those skilled in the art as a mobile station (MS), a subscriber station, a mobile unit, a subscriber unit, a wireless unit, a remote unit, a mobile device, a wireless device, a wireless communications device, a remote device, a mobile subscriber station, an access terminal (AT), a mobile terminal, a wireless terminal, a remote terminal, a handset, a terminal, a user agent, a mobile client, a client, or some other suitable terminology. For illustrative purposes, three UEs 110 are shown in communication with the node Bs 108. The downlink (DL), also called the forward link, refers to the communication link from a node B to a UE, and the uplink (UL), also called the reverse link, refers to the communication link from a UE to a node B.

The core network 104, as shown, includes a GSM core network. However, as those skilled in the art will recognize, the various concepts presented throughout this disclosure may be implemented in a RAN, or other suitable access network, to provide UEs with access to types of core networks other than GSM networks.

In this example, the core network 104 supports circuit-switched services with a mobile switching center (MSC) 112 and a gateway MSC (GMSC) 114. One or more RNCs, such as the RNC 106, may be connected to the MSC 112. The MSC 112 is an apparatus that controls call setup, call routing, and UE mobility functions. The MSC 112 also includes a visitor location register (VLR) (not shown) that contains subscriber-related information for the duration that a UE is in the coverage area of the MSC 112. The GMSC 114 provides a gateway through the MSC 112 for the UE to access a circuit-switched network 116. The GMSC 114 includes a home location register (HLR) (not shown) containing subscriber data, such as the data reflecting the details of the services to which a particular user has subscribed. The HLR is also associated with an authentication center (AuC) that contains subscriber-specific authentication data. When a call is received for a particular UE, the GMSC 114 queries the HLR to determine the UE's location and forwards the call to the particular MSC serving that location.

The core network 104 also supports packet-data services with a serving GPRS support node (SGSN) 118 and a gateway GPRS support node (GGSN) 120. GPRS, which stands for General Packet Radio Service, is designed to provide packet-data services at speeds higher than those available with standard GSM circuit-switched data services. The GGSN 120 provides a connection for the RAN 102 to a packet-based network 122. The packet-based network 122 may be the Internet, a private data network, or some other suitable packet-based network. The primary function of the GGSN 120 is to provide the UEs 110 with packet-based network connectivity. Data packets are transferred between the GGSN 120 and the UEs 110 through the SGSN 118, which performs primarily the same functions in the packet-based domain as the MSC 112 performs in the circuit-switched domain.

The UMTS air interface is a spread spectrum Direct-Sequence Code Division Multiple Access (DS-CDMA) system. The spread spectrum DS-CDMA spreads user data over a much wider bandwidth through multiplication by a sequence of pseudorandom bits called chips. The TD-SCDMA standard is based on such direct sequence spread spectrum technology and additionally calls for a time division duplexing (TDD), rather than a frequency division duplexing (FDD) as used in many FDD mode UMTS/W-CDMA systems. TDD uses the same carrier frequency for both the uplink (UL) and downlink (DL) between a node B 108 and a UE 110, but divides uplink and downlink transmissions into different time slots in the carrier.

Figure 2:
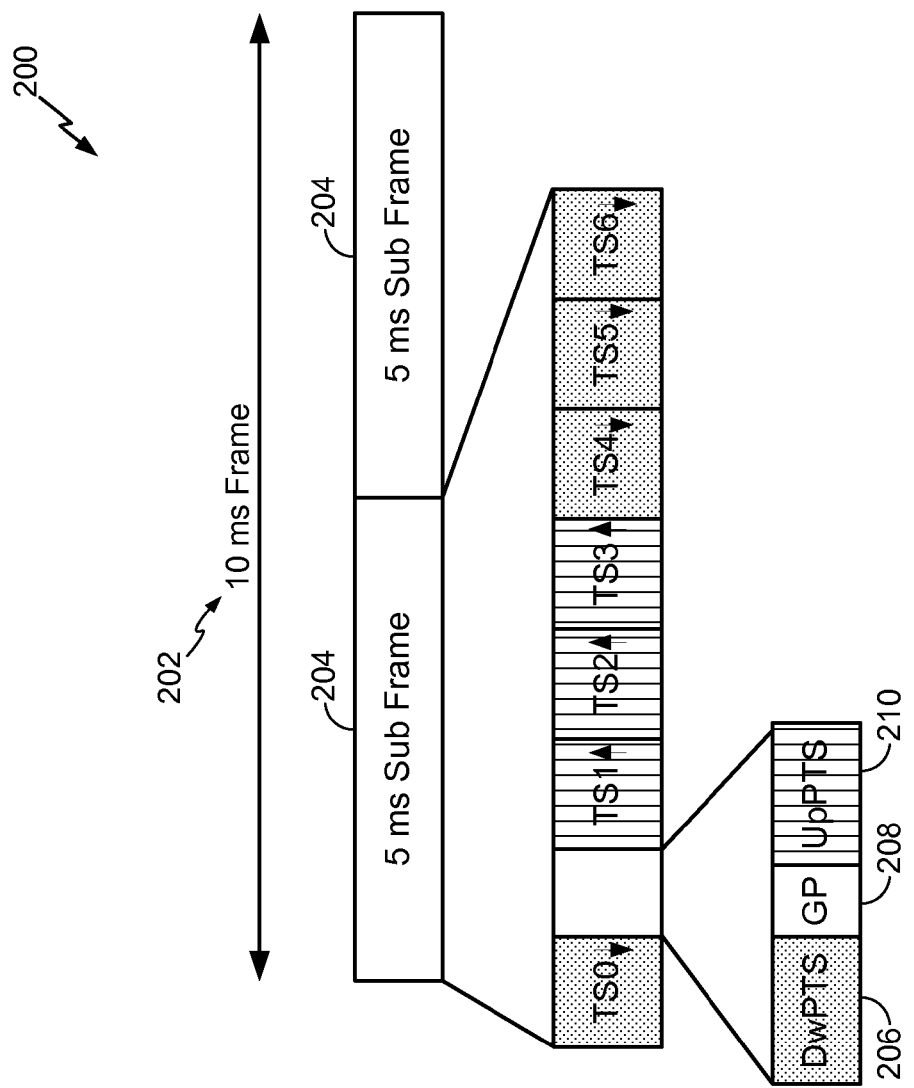
FIG. 2 is a block diagram conceptually illustrating an example of a frame structure in a telecommunications system.

FIG. 2 shows a frame structure 200 for a TD-SCDMA carrier. The TD-SCDMA carrier, as illustrated, has a frame 202 that is 10 ms in length. The frame 202 has two 5 ms subframes 204, and each of the subframes 204 includes seven time slots, TS0 through TS6. The first time slot, TS0, is usually allocated for downlink communication, while the second time slot, TS1, is usually allocated for uplink communication. The remaining time slots, TS2 through TS6, may be used for either uplink or downlink, which allows for greater flexibility during times of higher data transmission times in either the uplink or downlink directions. A downlink pilot time slot (DwPTS) 206 (also referred to herein as the downlink pilot channel (DwPCH)), a guard period (GP) 208, and an uplink pilot time slot (UpPTS) 210 (also referred to herein as the uplink pilot channel (UpPCH)) are located between TS0 and TS1. Each time slot, TS0-TS6, may allow data transmission multiplexed on a maximum of 16 code channels.

Figure 3:
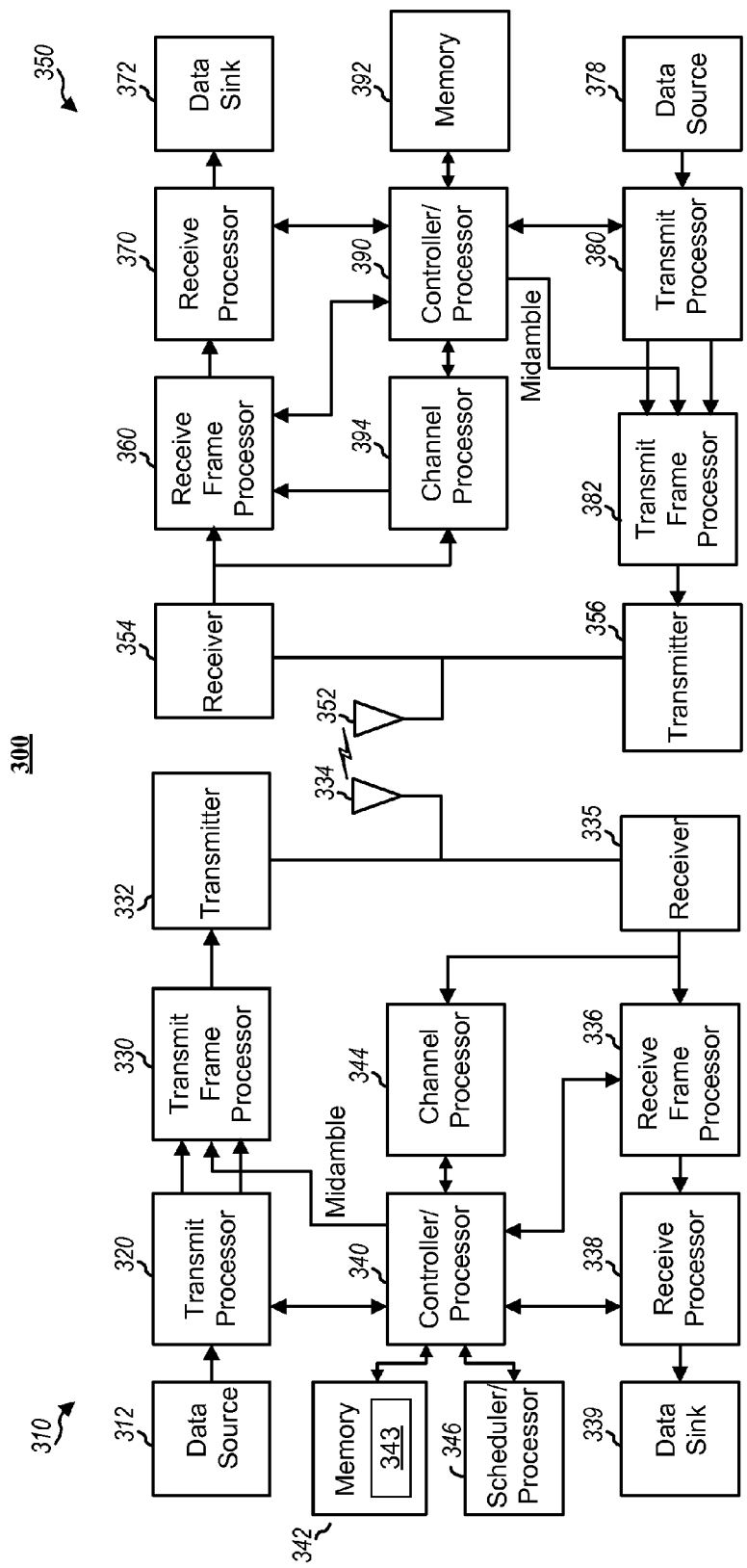
FIG. 3 is a block diagram conceptually illustrating an example of a node B in communication with a UE in a telecommunications system.

FIG. 3 is a block diagram of a node B 310 in communication with a UE 350 in a RAN 300, where the RAN 300 may be the RAN 102 in FIG. 1, the node B 310 may be the node B 108 in FIG. 1, and the UE 350 may be the UE 110 in FIG. 1. In the downlink communication, a transmit processor 320 may receive data from a data source 312 and control signals from a controller/processor 340. The transmit processor 320 provides various signal processing functions for the data and control signals, as well as reference signals (e.g., pilot signals). For example, the transmit processor 320 may provide cyclic redundancy check (CRC) codes for error detection, coding and interleaving to facilitate forward error correction (FEC), mapping to signal constellations based on various modulation schemes (e.g., binary phase-shift keying (BPSK), quadrature phase-shift keying (QPSK), M-phase-shift keying (M-PSK), M-quadrature amplitude modulation (M-QAM), and the like), spreading with orthogonal variable spreading factors (OVSF), and multiplying with scrambling codes to produce a series of symbols. Channel estimates from a channel processor 344 may be used by a controller/processor 340 to determine the coding, modulation, spreading, and/or scrambling schemes for the transmit processor 320. These channel estimates may be derived from a reference signal transmitted by the UE 350 or from feedback contained in the midamble from the UE 350. The symbols generated by the transmit processor 320 are provided to a transmit frame processor 330 to create a frame structure. The transmit frame processor 330 creates this frame structure by multiplexing the symbols with a midamble from the controller/processor 340, resulting in a series of frames. The frames are then provided to a transmitter 332, which provides various signal conditioning functions including amplifying, filtering, and modulating the frames onto a carrier for downlink transmission over the wireless medium through smart antennas 334. The smart antennas 334 may be implemented with beam steering bidirectional adaptive antenna arrays or other similar beam technologies.

At the UE 350, a receiver 354 receives the downlink transmission through an antenna 352 and processes the transmission to recover the information modulated onto the carrier. The information recovered by the receiver 354 is provided to a receive frame processor 360, which parses each frame, and provides the midamble to a channel processor 394 and the data, control, and reference signals to a receive processor 370. The receive processor 370 then performs the inverse of the processing performed by the transmit processor 320 in the node B 310. More specifically, the receive processor 370 descrambles and despreads the symbols, and then determines the most likely signal constellation points transmitted by the node B 310 based on the modulation scheme. These soft decisions may be based on channel estimates computed by the channel processor 394. The soft decisions are then decoded and deinterleaved to recover the data, control, and reference signals. The CRC codes are then checked to determine whether the frames were successfully decoded. The data carried by the successfully decoded frames will then be provided to a data sink 372, which represents applications running in the UE 350 and/or various user interfaces (e.g., display). Control signals carried by successfully decoded frames will be provided to a controller/processor 390. When frames are unsuccessfully decoded by the receiver processor 370, the controller/processor 390 may also use an acknowledgement (ACK) and/or negative acknowledgement (NACK) protocol to support retransmission requests for those frames.

In the uplink, data from a data source 378 and control signals from the controller/processor 390 are provided to a transmit processor 380. The data source 378 may represent applications running in the UE 350 and various user interfaces (e.g., keyboard, pointing device, track wheel, and the like). Similar to the functionality described in connection with the downlink transmission by the node B 310, the transmit processor 380 provides various signal processing functions including CRC codes, coding and interleaving to facilitate FEC, mapping to signal constellations, spreading with OVSFs, and scrambling to produce a series of symbols. Channel estimates, derived by the channel processor 394 from a reference signal transmitted by the node B 310 or from feedback contained in the midamble transmitted by the node B 310, may be used to select the appropriate coding, modulation, spreading, and/or scrambling schemes. The symbols produced by the transmit processor 380 will be provided to a transmit frame processor 382 to create a frame structure. The transmit frame processor 382 creates this frame structure by multiplexing the symbols with a midamble from the controller/processor 390, resulting in a series of frames. The frames are then provided to a transmitter 356, which provides various signal conditioning functions including amplification, filtering, and modulating the frames onto a carrier for uplink transmission over the wireless medium through the antenna 352.

The uplink transmission is processed at the node B 310 in a manner similar to that described in connection with the receiver function at the UE 350. A receiver 335 receives the uplink transmission through the smart antennas 334 and processes the transmission to recover the information modulated onto the carrier. The information recovered by the receiver 335 is provided to a receive frame processor 336, which parses each frame, and provides the midamble to the channel processor 344 and the data, control, and reference signals to a receive processor 338. The receive processor 338 performs the inverse of the processing performed by the transmit processor 380 in the UE 350. The data and control signals carried by the successfully decoded frames may then be provided to a data sink 339 and the controller/processor 340, respectively. If some of the frames were unsuccessfully decoded by the receive processor 338, the controller/processor 340 may also use an acknowledgement (ACK) and/or negative acknowledgement (NACK) protocol to support retransmission requests for those frames.

The controller/processors 340 and 390 may be used to direct the operation at the node B 310 and the UE 350, respectively. For example, the controller/processors 340 and 390 may provide various functions including timing, peripheral interfaces, voltage regulation, power management, and other control functions. The computer readable media of memories 342 and 392 may store data and software for the node B 310 and the UE 350, respectively. For example, the memory 392 of the UE 350 may store a pilot recognition module that, when executed by the controller/processor 390, allows the UE 350 to identify and process a control channel, such as a downlink pilot channel (DwPCH), received on one or more secondary carrier frequencies. Similarly, the memory 342 of the node B 310 may store a pilot module 343 that, when executed by the controller/processor 340, configures the node B 310 to transmit a control channel, such as a downlink pilot channel (DwPCH), on each carrier frequency of the multicarrier network. The memory 342 of the node B 310 may also store a control channel interference reduction module that, when executed by the controller/processor 340, allows the node B 310 to reduce or minimize interference between the DwPCH on different transmission carrier frequencies. A scheduler/processor 346 at the node B 310 may be used to allocate resources to the UEs and schedule downlink and/or uplink transmissions for the UEs.

Figure 4:
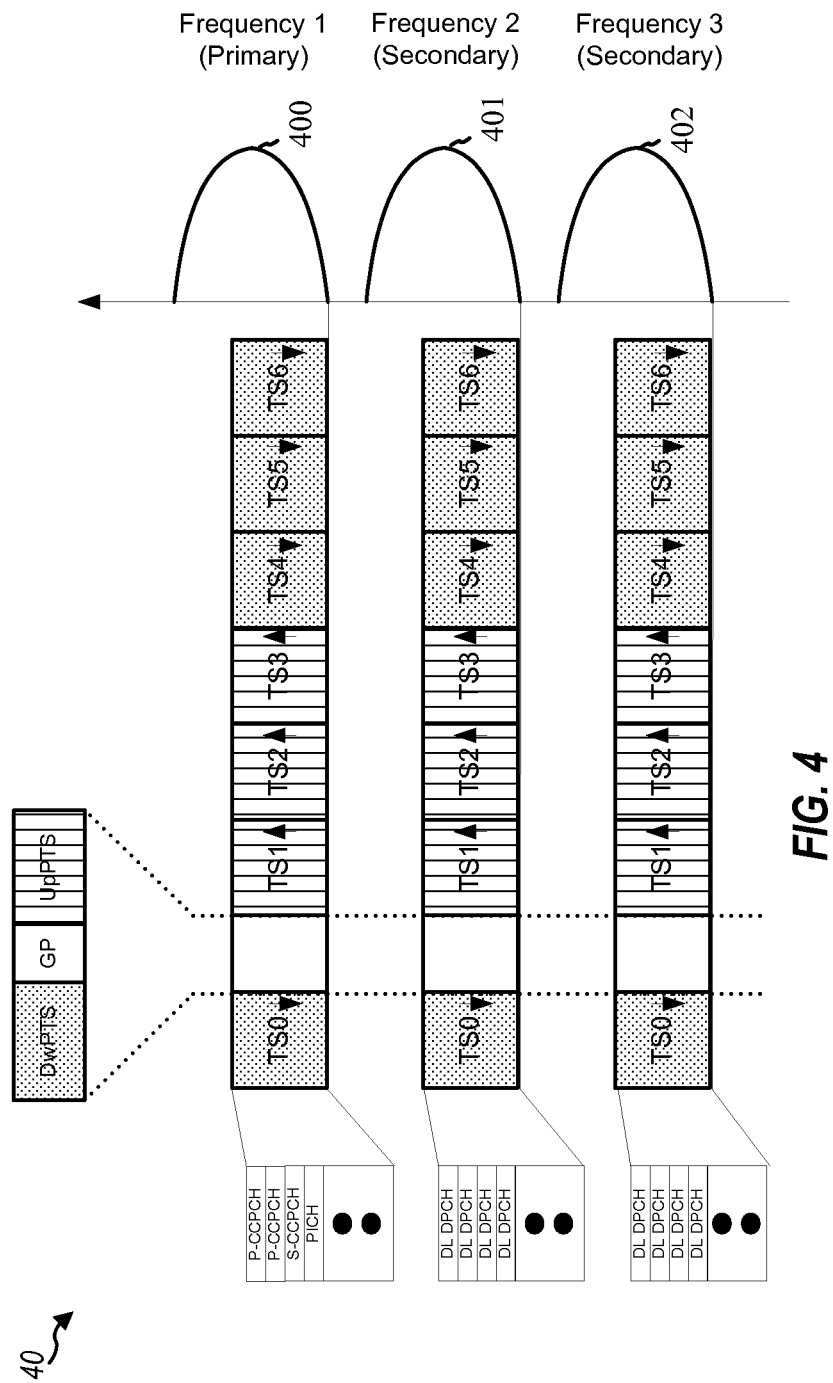
FIG. 4 is a block diagram conceptually illustrating carrier frequencies in a multi-carrier TD-SCDMA communication system.

In order to provide more capacity, the TD-SCDMA system may allow multiple carrier signals or frequencies. Assuming that N is the total number of carriers, the carrier frequencies may be represented by the set $\{F(i), i=0, 1, \ldots, N-1\}$, where the carrier frequency, F(0), is the primary carrier frequency and the rest are secondary carrier frequencies. For example, a cell can have three carrier signals whereby the data can be transmitted on some code channels of a time slot on one of the three carrier signal frequencies. FIG. 4 is a block diagram conceptually illustrating carrier frequencies 40 in a multi-carrier TD-SCDMA communication system. The multiple carrier frequencies include a primary carrier frequency 400 (F(1)), and two secondary carrier frequencies 401 and 402 (F(2) and F(3)). In such multi-carrier systems, the system overhead is transmitted on the first time slot (TS0) of the primary carrier frequency 400. In the first time slot (TS0) of the primary carrier frequency 400, the Primary Common Control Physical Channel (P-CCPCH), the Secondary Common Control Physical Channel (S-CCPCH), the Paging Indicator Channel (PICH), and the like are transmitted. The traffic channels (e.g., Downlink Dedicated Physical Channels (DL DPCHs)) may then be carried on the remaining time slots (TS4-TS6) of the primary carrier frequency 400 and on all downlink time slots (TS0 and TS4-TS6) of the secondary carrier frequencies 401 and 402. Therefore, in such configurations, a UE will receive system information and monitor the paging messages on the primary carrier frequency 400 while transmitting and receiving data on either one or all of the primary carrier frequency 400 and the secondary carrier frequencies 401 and 402.

TD-SCDMA employs time division and code division techniques to allow multiple UEs to share the same radio bandwidth on a particular frequency channel. The bandwidth of each frequency channel in TD-SCDMA system is 1.6 MHz, operating at 1.28 Mega chips per second. The downlink and uplink transmissions share the same bandwidth in different time slots. In each time slot, there are multiple code channels. As shown in FIG. 4 there is one downlink (DL) timeslot TS0, followed by three uplink (UL) timeslots TS1-TS3, and followed by three DL timeslots TS4-TS6. Between TS0 and TS1, there are Downlink Pilot Time Slot (DwPTS) and Uplink Pilot Time Slot (UpPTS), separated by a gap GP. The DwPTS is used to transmit the Downlink Pilot Channel (DwPCH) where the node B (NB) sends the downlink synchronization (SYNC_DL) code. Because TD-SCDMA is synchronous, the timeslots for each frequency are aligned. In other words, TS0 occurs at the same time for each frequency, TS1 occurs at the same time for each frequency, etc.

Figure 5:
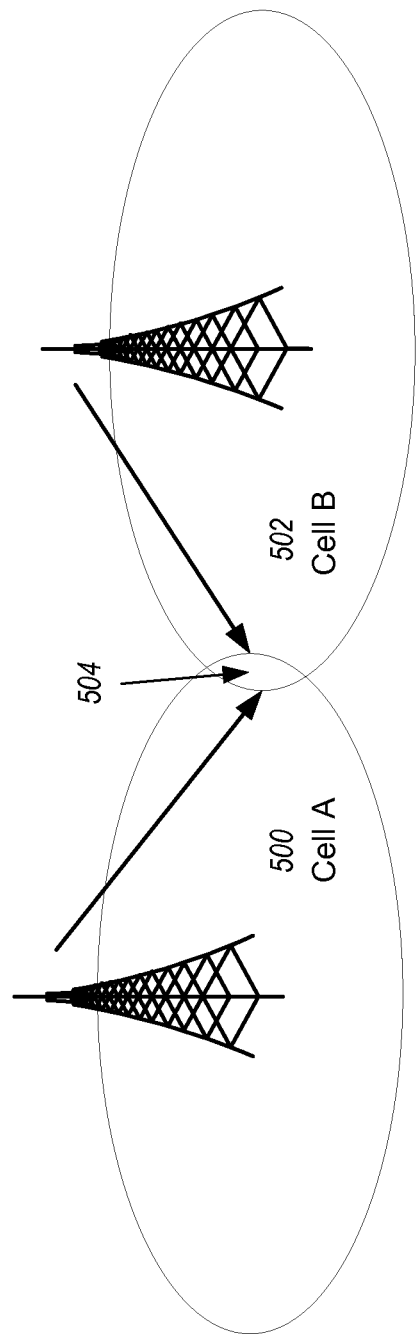
FIG. 5 is a diagram conceptually illustrating a multi-carrier TD-SCDMA communication system.

It should be noted that system control channels, such as the P-CCPCH (Primary Common Control Physical Channel), S-CCPCH ((Secondary Common Control Physical Channel), PICH (Pilot Indicator Channel) may be configured on the primary carrier frequency 400. However the DwPTS is not transmitted on the secondary carriers to reduce interference between adjacent cells, which can have different frequency channels for their primary carrier but may have overlapping frequency channels with respect to the secondary carriers. FIG. 5 illustrates how adjacent Cell A 500 and Cell B 502 can have overlap 504 in their transmission regions. In this example, if Cell B 502 transmits the DwPCH on the secondary carrier, the transmission could interfere with the DwPCH of the primary carrier of Cell A 500.

Figure 6:
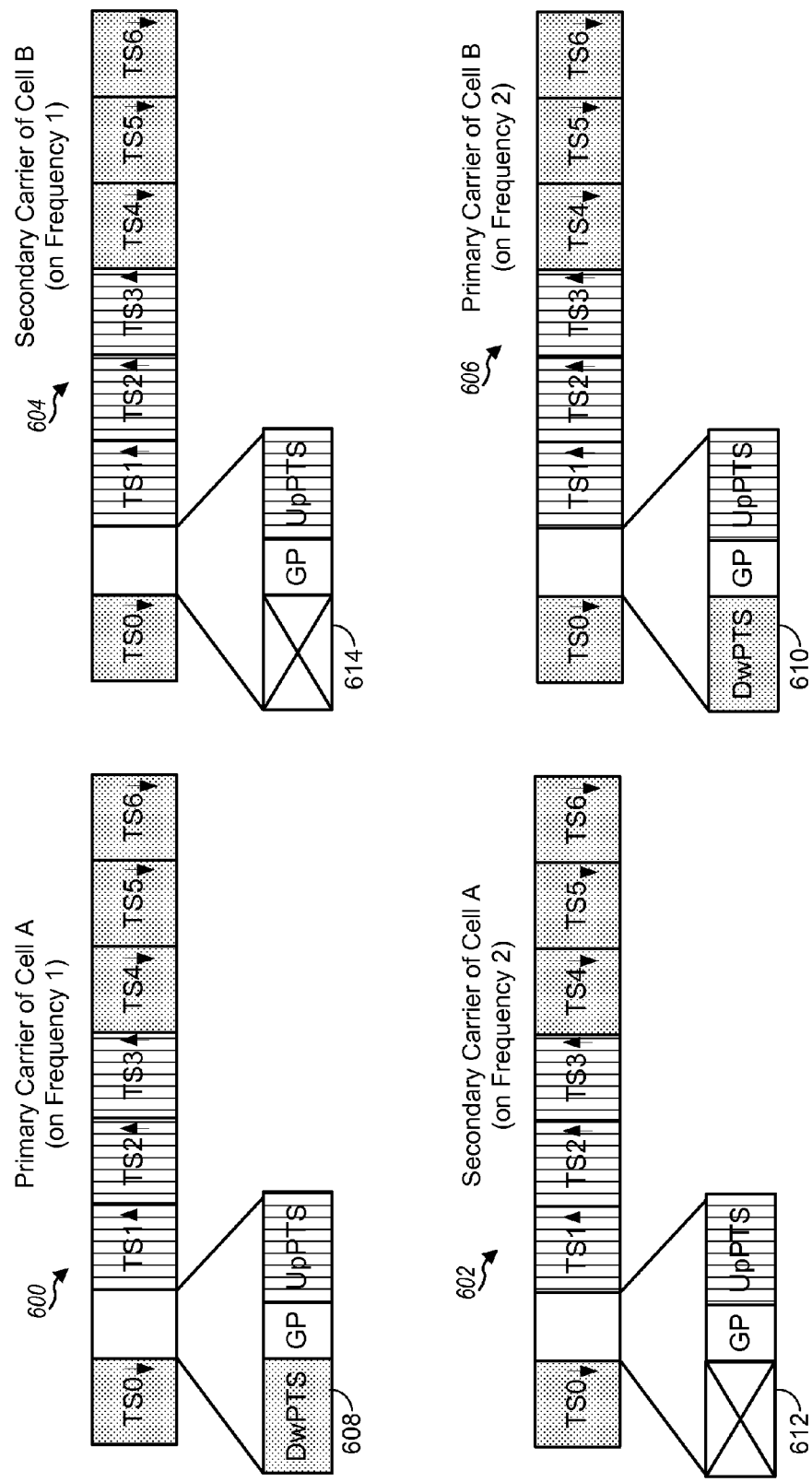
FIG. 6 is a block diagram conceptually illustrating carrier frequencies in a multi-carrier TD-SCDMA communication system.

To avoid interference with overhead channel transmission, DwPCH transmission is conventionally configured as shown in FIG. 6. FIG. 6 illustrates DwPCH transmission using the example of two cells, each cell having a primary carrier frequency and one secondary carrier frequency. In the illustration, Cell A's primary carrier frequency is Frequency 1 and its secondary carrier frequency is Frequency 2. In the illustration, Cell B's primary carrier frequency is Frequency 2 and its primary carrier frequency is Frequency 1. Transmission block 600 illustrates the signal transmitted on Cell A's primary carrier frequency. Transmission block 602 illustrates the transmission on Cell A's secondary carrier frequency. Transmission block 606 illustrates the transmission on Cell B's primary carrier frequency. Transmission block 604 illustrates the signal transmitted on Cell B's secondary carrier frequency.

Cell A transmits its DwPTS on its primary carrier frequency, as shown in block 608. Cell B transmits its DwPTS on its primary carrier frequency, as shown in block 610. To avoid interference, Cell A does not transmit its DwPTS on its secondary carrier frequency, as shown in block 612. Similarly, to avoid interference, Cell B does not transmit its DwPTS on its secondary carrier frequency, as shown in block 614.

However, the DwPCH on the secondary carrier would provide very useful information, such as signal strength or quality of the secondary carrier. Therefore, optimal or even improved resource allocation is difficult without transmitting the DwPCH on secondary carriers. The present disclosure allows DwPCH transmission on secondary carriers while reducing or minimizing interference.

According to one aspect, DwPCH transmission on one or more secondary carrier frequencies occurs only during one subframe out of every set of subframes to avoid interference that can occur when transmitting the DwPCH on secondary carriers during every subframe. The node B of each cell transmits the DwPCH on system subframe number k, as follows:

$$k \bmod \text{Period} = \text{Offset}$$

where the parameter Period is the period expressed in number of subframes, and Offset indicates the subframe within the period to transmit the DwPCH. In one embodiment, each subframe can have a subframe number from 0 to 8191.

Because the DwPCH is only transmitted during one subframe within the period, the interference caused by transmission of the DwPCH on a secondary carrier frequency is reduced. To further smooth the interference in the time domain between neighbor cells, varying Offset values can be used. Offset values can be different for the multiple secondary carriers of a cell.

Figure 7:
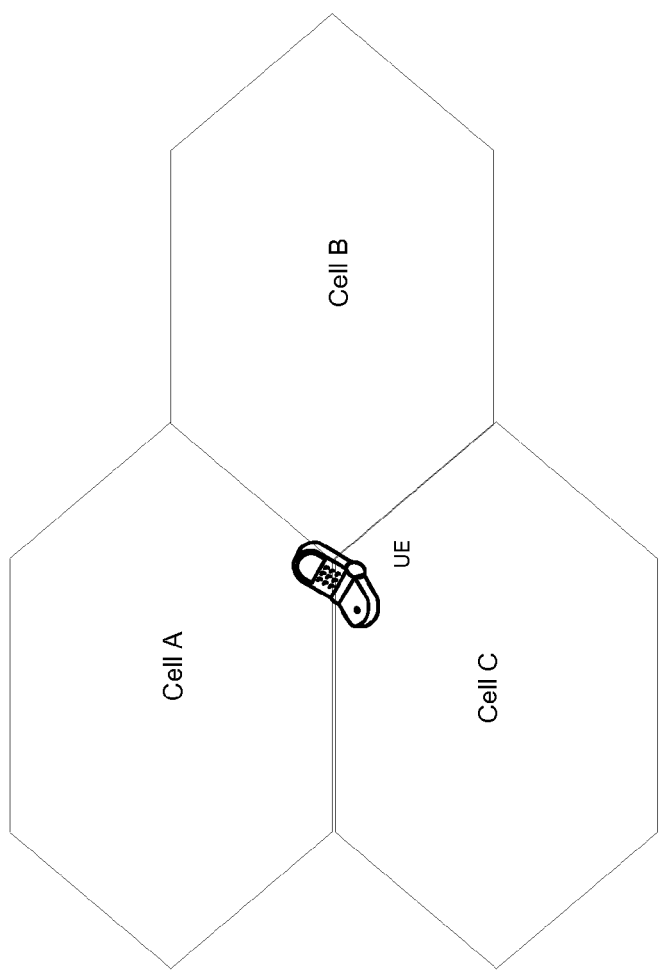
FIG. 7 is a diagram conceptually illustrating a multi-carrier TD-SCDMA communication system.
Figure 8:
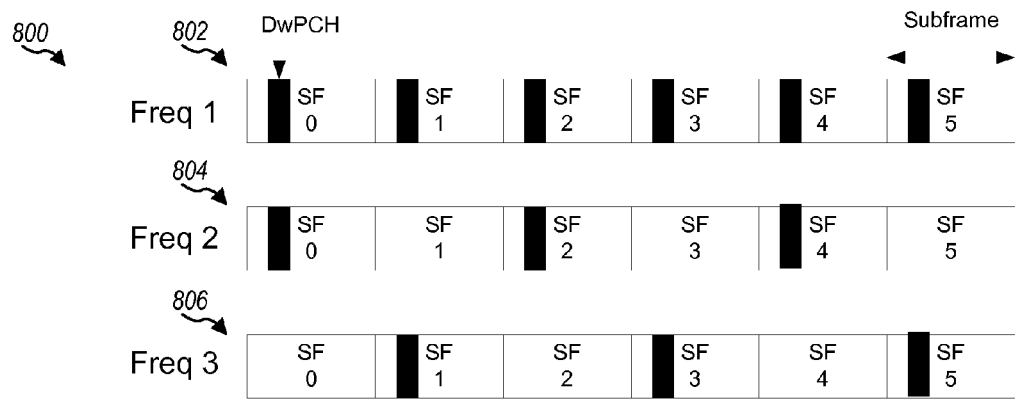
FIG. 8 is a block diagram conceptually illustrating multi-carrier communications in a TD-SCDMA communication system according to one aspect of the present disclosure.
Figure 8:
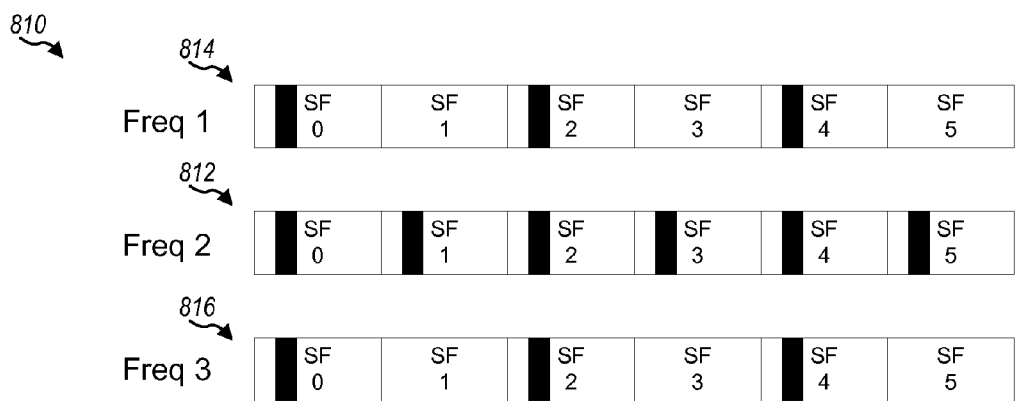
Figure 8:
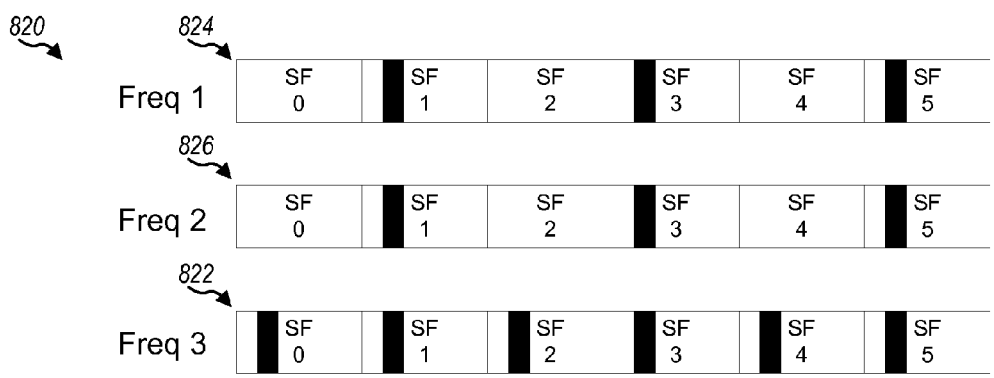

FIG. 7 illustrates an example of a network segment showing a three cell transmission area where each cell transmits to UEs on three carrier frequencies (one primary and two secondary), and each cell has a different primary carrier frequency, which overlaps with the secondary carrier frequencies of the other two cells. FIG. 8 shows example transmission blocks in the network segment of FIG. 7 where the Period is set to 2 and the Offset is selected to evenly distribute the subframes when the DwPCH is transmitted on the secondary frequencies.

As shown in Cell A's transmissions 800, Cell A uses Frequency 1 as its primary carrier and broadcasts its DwPCH every subframe on Frequency 1 as shown in block 802. On Frequency 2 (one of Cell A's secondary carriers) Cell A broadcasts its DwPCH with a Period 2 and Offset 0, so at subframes 0, 2, 4, etc. as shown in block 804. On Frequency 3 (another one of Cell A's secondary carriers) Cell A broadcasts its DwPCH with a Period 2 and Offset 1, so at subframes 1, 3, 5, etc. as shown in block 806.

As shown in Cell B's transmissions 810, Cell B uses Frequency 2 as its primary carrier and broadcasts its DwPCH every subframe on Frequency 2 as shown in block 812. On Frequency 1 (one of Cell B's secondary carriers) Cell B broadcasts its DwPCH with a Period 2 and Offset 0, so at subframes 0, 2, 4, etc. as shown in block 814. On Frequency 3 (another one of Cell B's secondary carriers) Cell B also broadcasts its DwPCH with a Period 2 and Offset 0, so at subframes 0, 2, 4, etc. as shown in block 816.

As shown in Cell C's transmissions 820, Cell C uses Frequency 3 as its primary carrier and broadcasts its DwPCH every subframe on Frequency 3 as shown in block 822. On Frequency 1 (one of Cell C's secondary carriers) Cell C broadcasts its DwPCH with a Period 2 and Offset 1, so at subframes 1, 3, 5, etc. as shown in block 824 On Frequency 2 (another one of Cell C's secondary carriers) Cell C also broadcasts its DwPCH with a Period 2 and Offset 1, so at subframes 1, 3, 5, etc. as shown in block 826.

As shown in FIG. 9, in the example of FIG. 8, Cell A broadcasts its DwPCH on secondary channels with an alternating offset of 0 or 1 where Cell B always uses an offset of 0 and Cell C always uses an offset of 1.

In this illustrated manner, in each subframe a particular frequency has only two DwPCH signals being transmitted at the same time, one by the cell using the frequency as a primary carrier, the other by a cell using the frequency as a secondary carrier. This method reduces or minimizes interference from multiple cells broadcasting the DwPCH on secondary carriers. The above example is illustrative. The period value can be set larger in order to increase the spatial reuse factor.

In one embodiment, the offset and period parameters are broadcast in the System Information. For example, the System Information transmitted via the P-CCPCH on the primary carrier can indicate the Offset and Period of each of the secondary carriers. In this manner a UE can receive the Offset and Period in the broadcast and adjust its obtaining of control channels accordingly. In another embodiment, the parameter values are not broadcast. In this embodiment, the UE acquires and identifies the Period and Offset parameters by detecting them using the SYNC_DL code on the subframe of the secondary carrier. Of course, other ways of obtaining the parameter values are contemplated.

Once the Period and Offset are known, the UE can perform a measurement of the DwPCH signal and provide a measurement report of each carrier frequency to the node B for resource allocation purposes.

Figure 10:
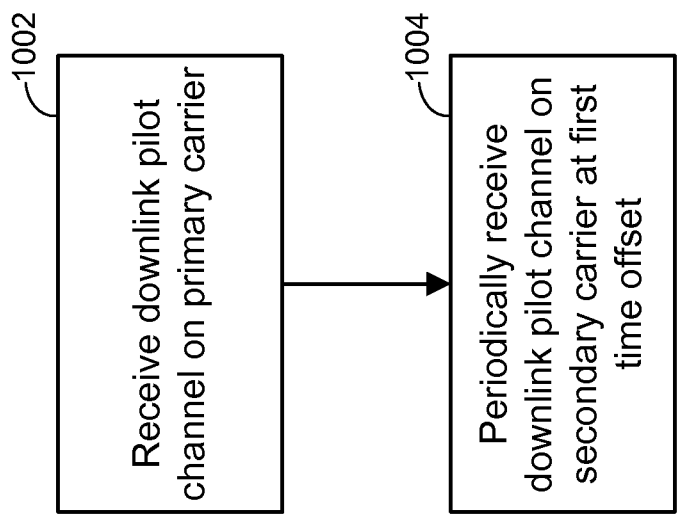
FIG. 10 is a flow diagram illustrating multi-carrier communications in a TD-SCDMA communication system according to one aspect of the present disclosure.

FIG. 10 is a flow diagram illustrating multi-carrier communications in a TD-SCDMA communication system according to one aspect of the present disclosure. An apparatus, such as the UE 110, is configured to regularly receive a DwPCH on a primary carrier frequency at block 1002. At block 1004 the UE periodically receives the DwPCH on a secondary carrier frequency with a first time offset. The period is longer than a single subframe so that the DwPCH on the secondary carrier is not received during every single subframe. The apparatus may also be configured to receive a DwPCH on at least one secondary carrier frequency with a similar or different period and offset relative to other secondary carrier frequencies.

In one configuration, the apparatus, such as the node B 310, is configured for wireless communication includes means for transmitting the DwPCH on a secondary carrier frequency using a particular period and offset. In one aspect, the aforementioned means may be the antennas 334, the transmitter 332, the transmit frame processor 330, the channel processor 344, the transmit processor 320, the controller/processor 340, and the memory 342 storing a pilot module 343 all of which are configured together to perform the functions recited by the aforementioned means. In another aspect, the aforementioned means may be a module or any apparatus configured to perform the functions recited by the aforementioned means.

Several aspects of a telecommunications system have been presented with reference to a TD-SCDMA system. As those skilled in the art will readily appreciate, various aspects described throughout this disclosure may be extended to other telecommunication systems, network architectures and communication standards. By way of example, various aspects may be extended to other UMTS systems such as W-CDMA, High Speed Downlink Packet Access (HSDPA), High Speed Uplink Packet Access (HSUPA), High Speed Packet Access Plus (HSPA+) and TD-CDMA. Various aspects may also be extended to systems employing Long Term Evolution (LTE) (in FDD, TDD, or both modes), LTE-Advanced (LTE-A) (in FDD, TDD, or both modes), CDMA2000, Evolution-Data Optimized (EV-DO), Ultra Mobile Broadband (UMB), IEEE 802.11 (Wi-Fi), IEEE 802.16 (WiMAX), IEEE 802.20, Ultra-Wideband (UWB), Bluetooth, and/or other suitable systems. The actual telecommunication standard, network architecture, and/or communication standard employed will depend on the specific application and the overall design constraints imposed on the system.

Several processors have been described in connection with various apparatuses and methods. These processors may be implemented using electronic hardware, computer software, or any combination thereof. Whether such processors are implemented as hardware or software will depend upon the particular application and overall design constraints imposed on the system. By way of example, a processor, any portion of a processor, or any combination of processors presented in this disclosure may be implemented with a microprocessor, microcontroller, digital signal processor (DSP), a field-programmable gate array (FPGA), a programmable logic device (PLD), a state machine, gated logic, discrete hardware circuits, and other suitable processing components configured to perform the various functions described throughout this disclosure. The functionality of a processor, any portion of a processor, or any combination of processors presented in this disclosure may be implemented with software being executed by a microprocessor, microcontroller, DSP, or other suitable platform.

Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, memory such as a magnetic storage device (e.g., hard disk, floppy disk, magnetic strip), an optical disk (e.g., compact disc (CD), digital versatile disc (DVD)), a smart card, a flash memory device (e.g., card, stick, key drive), random access memory (RAM), read only memory (ROM), programmable ROM (PROM), erasable PROM (EPROM), electrically erasable PROM (EEPROM), a register, or a removable disk. Although memory is shown separate from the processors in the various aspects presented throughout this disclosure, the memory may be internal to the processors (e.g., cache or register).

Computer-readable media may be embodied in a computer-program product. By way of example, a computer-program product may include a computer-readable medium in packaging materials. Those skilled in the art will recognize how best to implement the described functionality presented throughout this disclosure depending on the particular application and the overall design constraints imposed on the overall system.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method of wireless communication, comprising:
   receiving a downlink pilot channel (DwPCH) transmitted on a primary carrier during every subframe; and
   periodically receiving the downlink pilot channel on a secondary carrier at a first time offset, a period for the receiving being longer than one subframe.

2. The method of claim 1, further comprising periodically receiving the downlink pilot channel on at least one second secondary carrier based on at least one second time offset.

3. The method of claim 2, in which the at least one second time offset differs from the first time offset.

4. The method of claim 2, in which the at least one second time offset is the same as the first time offset.

5. The method of claim 2, in which the at least one second time offset comprises a plurality of time offsets, at least one of the plurality being the same as the first time offset, at least one of the plurality being different from the first time offset.

6. The method of claim 1 further comprising receiving a broadcast communication comprising the period and the first time offset.

7. The method of claim 1 further comprising determining the period and offset from a secondary carrier communication.

8. The method of claim 1, in which the primary carrier and secondary carrier are in a time division-synchronous code division multiple access (TD-SCDMA) network.

9. A user equipment (UE) configured for wireless communication in a multicarrier radio access network, the UE comprising:
   means for receiving a downlink pilot channel transmitted on a primary carrier during every subframe; and
   means for periodically receiving the downlink pilot channel on a secondary carrier at a first time offset, a period for the receiving being longer than one subframe.

10. The UE of claim 9 further comprising means for periodically receiving the downlink pilot channel on at least one second secondary carrier based on at least one second time offset.

11. The UE of claim 10, in which the at least one second time offset differs from the first time offset.

12. The UE of claim 9 further comprising means for receiving a broadcast communication comprising the period and the first time offset.

13. The UE of claim 9 further comprising means for determining the period and offset from a secondary carrier communication.

14. The UE of claim 9, in which the primary carrier and secondary carrier are in a time division-synchronous code division multiple access (TD-SCDMA) network.

15. A computer program product, comprising:
   a non-transitory computer readable medium having program code recorded thereon, the program code when executed by a computer cause the computer to:
      receive a downlink pilot channel transmitted on a primary carrier during every subframe; and
      periodically receive the downlink pilot channel on a secondary carrier at a first time offset, a period for the receiving being longer than one subframe.

16. The computer program product of claim 15, the program code when executed by the computer further causing the computer to periodically receive the downlink pilot channel on at least one second secondary carrier based on at least one second time offset.

17. The computer program product of claim 16, in which the at least one second time offset differs from the first time offset.

18. The computer program product of claim 15, the program code when executed by the computer further causing the computer to receive a broadcast communication comprising the period and the first time offset.

19. The computer program product of claim 15, the program code when executed by the computer further causing the computer to determine the period and offset from a secondary carrier communication.

20. The computer program product of claim 15, in which the primary carrier and secondary carrier are in a time division-synchronous code division multiple access (TD-SCDMA) network.

21. A user equipment (UE) configured for wireless communication, the UE comprising:
   at least one processor; and
   a memory coupled to the at least one processor, wherein the at least one processor is configured:
      to receive a downlink pilot channel transmitted on a primary carrier during every subframe; and
      to periodically receive the downlink pilot channel on a secondary carrier at a first time offset, a period for the receiving being longer than one subframe.

22. The UE of claim 21, wherein the at least one processor is further configured to periodically receive the downlink pilot channel on at least one second secondary carrier based on at least one second time offset.

23. The UE of claim 22, in which the at least one second time offset differs from the first time offset.

24. The UE of claim 21, wherein the at least one processor is further configured to receive a broadcast communication comprising the period and the first time offset.

25. The UE of claim 21, wherein the at least one processor is further configured to determine the period and offset from a secondary carrier communication.

26. The UE of claim 21, in which the primary carrier and secondary carrier are in a time division-synchronous code division multiple access (TD-SCDMA) network.

27. A method of wireless communication, comprising:
   transmitting a downlink pilot channel (DwPCH) on a primary carrier during every subframe; and periodically transmitting the downlink pilot channel on a secondary carrier at a first time offset, a period for the transmitting being longer than one subframe.

28. The method of claim 27, further comprising periodically transmitting the downlink pilot channel on at least one second secondary carrier based on at least one second time offset.

29. The method of claim 28, in which the at least one second time offset differs from the first time offset.

30. The method of claim 28, in which the at least one second time offset is the same as the first time offset.

31. The method of claim 28, in which the at least one second time offset comprises a plurality of time offsets, at least one of the plurality being the same as the first time offset, at least one of the plurality being different from the first time offset.

32. The method of claim 27 further comprising transmitting a broadcast communication comprising the period and the first time offset.

33. The method of claim 27, in which the primary carrier and secondary carrier are in a time division-synchronous code division multiple access (TD-SCDMA) network.

34. A base station configured for wireless communication in a multicarrier radio access network, the base station comprising:
 means for transmitting a downlink pilot channel (DwPCH) on a primary carrier during every subframe; and
 means for periodically transmitting the downlink pilot channel on a secondary carrier at a first time offset, a period for the transmitting being longer than one subframe.

35. The base station of claim 34, further comprising means for periodically transmitting the downlink pilot channel on at least one second secondary carrier based on at least one second time offset.

36. The base station of claim 35, in which the at least one second time offset differs from the first time offset.

37. The base station of claim 35, in which the at least one second time offset is the same as the first time offset.

38. The base station of claim 35, in which the at least one second time offset comprises a plurality of time offsets, at least one of the plurality being the same as the first time offset, at least one of the plurality being different from the first time offset.

39. The base station of claim 34 further comprising means for transmitting a broadcast communication comprising the period and the first time offset.

40. The base station of claim 34, in which the primary carrier and secondary carrier are in a time division-synchronous code division multiple access (TD-SCDMA) network.

41. A computer program product, comprising:
 a non-transitory computer readable medium having program code recorded thereon, the program code when executed by a computer cause the computer to:
  transmit a downlink pilot channel (DwPCH) on a primary carrier during every subframe; and
  periodically transmit the downlink pilot channel on a secondary carrier at a first time offset, a period for the transmitting being longer than one subframe.

42. The computer program product of claim 41, the program code when executed by the computer further causing the computer to periodically transmit the downlink pilot channel on at least one second secondary carrier based on at least one second time offset.

43. The computer program product of claim 42, in which the at least one second time offset differs from the first time offset.

44. The computer program product of claim 42, in which the at least one second time offset is the same as the first time offset.

45. The computer program product of claim 42, in which the at least one second time offset comprises a plurality of time offsets, at least one of the plurality being the same as the first time offset, at least one of the plurality being different from the first time offset.

46. The computer program product of claim 41, the program code when executed by the computer further causing the computer to transmit a broadcast communication comprising the period and the first time offset.

47. The computer program product of claim 41, in which the primary carrier and secondary carrier are in a time division-synchronous code division multiple access (TD-SCDMA) network.

48. A base station configured for wireless communication, the base station comprising:
 at least one processor; and
 a memory coupled to the at least one processor, wherein the at least one processor is configured:
  to transmit a downlink pilot channel (DwPCH) on a primary carrier during every subframe; and
  to periodically transmit the downlink pilot channel on a secondary carrier at a first time offset, a period for the transmitting being longer than one subframe.

49. The base station of claim 48, wherein the at least one processor is further configured to periodically transmit the downlink pilot channel on at least one second secondary carrier based on at least one second time offset.

50. The base station of claim 49, in which the at least one second time offset differs from the first time offset.

51. The base station of claim 49, in which the at least one second time offset is the same as the first time offset.

52. The base station of claim 49, in which the at least one second time offset comprises a plurality of time offsets, at least one of the plurality being the same as the first time offset, at least one of the plurality being different from the first time offset.

53. The base station of claim 48, wherein the at least one processor is further configured to transmit a broadcast communication comprising the period and the first time offset.

54. The base station of claim 48, in which the primary carrier and secondary carrier are in a time division-synchronous code division multiple access (TD-SCDMA) network.

* * * * *